(12) United States Patent
Wright

(10) Patent No.: US 6,203,532 B1
(45) Date of Patent: *Mar. 20, 2001

(54) MULTI-DIAMETER MULTI-PURPOSE CANNULA CONNECTOR

(76) Inventor: John T. M. Wright, 555 S. Downing St., Denver, CO (US) 80209

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/303,881

(22) Filed: May 3, 1999

(51) Int. Cl.[7] ................................................ A61M 25/00
(52) U.S. Cl. .................. 604/264; 604/535; 604/905; 604/921
(58) Field of Search .................................. 604/264, 523, 604/533, 534, 535, 536, 905, 921

(56) References Cited

U.S. PATENT DOCUMENTS

| 3,339,551 | * | 9/1967 | Stoutenburgh | 604/535 X |
| 3,707,972 | * | 1/1973 | Villari et al. | 604/535 X |
| 4,511,163 | * | 4/1985 | Harris et al. | 604/535 |
| 4,774,940 | * | 10/1988 | Linder | 604/535 X |
| 5,637,102 | * | 6/1997 | Tolkoff et al. | 604/535 |

* cited by examiner

Primary Examiner—John D. Yasko

(57) ABSTRACT

A multi-diameter, multi-purpose cannula connector for connection to vessels of different sizes and suitable for use in coronary artery bypass graft surgery comprising small flexible cannula with several graduated diameter flanges located adjacent the proximal end is disclosed.

5 Claims, 1 Drawing Sheet

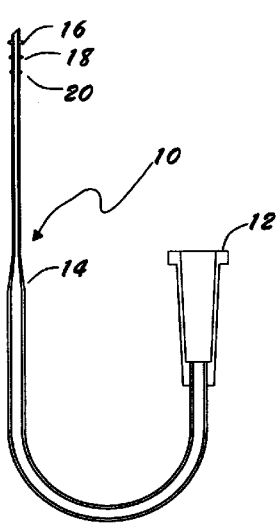
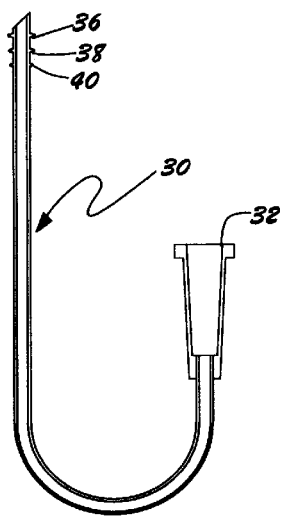
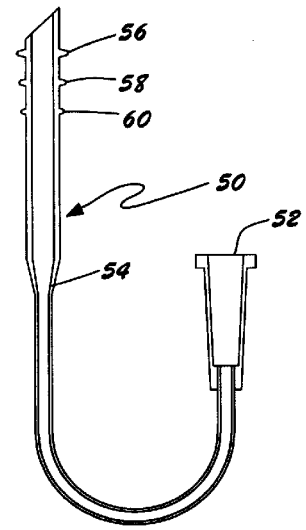
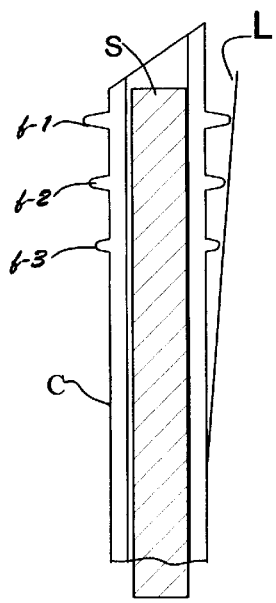
Fig. 1a
Fig. 2a
Fig. 3a
Fig. 4
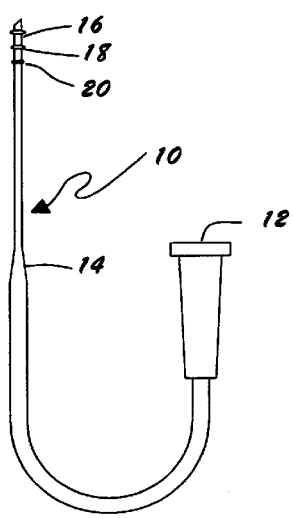
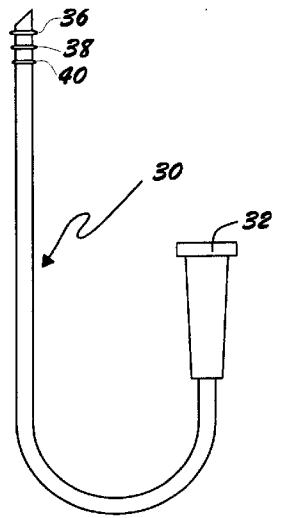
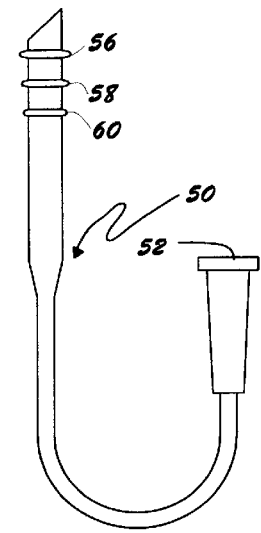
Fig. 1b
Fig. 2b
Fig. 3b

MULTI-DIAMETER MULTI-PURPOSE CANNULA CONNECTOR

FIELD OF THE INVENTION

This invention relates to a cannula used in surgery to divert blood from a patient's blood vessels to a separate device, to shunt a patient's blood from one blood vessel to another blood vessel or to infuse a solution into the patient's blood vessel.

BACKGROUND OF THE INVENTION

Many cardiovascular surgical procedures require that the patient's blood flow be diverted from a vein or artery to a blood treating or flow supporting device. Infusion of particular solutions or liquids into the patient's vascular system is essential to the success of many important cardiovascular procedures. Techniques and methods of using cannulas of many sizes and materials are well known in the art.

In spite of the many years of use of cannulas in surgery and the hundreds of cannula connectors and fittings, the problem of having readily at hand cannulas of the proper size to interconnect with each other, to permit a change in the size of the cannula and to permit the cannula to be introduced into and retained by a blood vessel remains. It is common to provide a cannula fitting which has one or more tapered ridges of the same diameter proximate the end of and extending from the surface of the cannula for being inserted into another cannula. A cannula fitting of this type is illustrated in, for example, U.S. Pat. No. 4,883,455 to Leonard, Nov. 28, 1989. Another type of cannula connector that comprises a double-tapered enlargement is shown in U.S. Pat. No. 4,323,072 to Rosenbluth et. al., Apr. 6, 1982. For many applications, no special structure is required to form a liquid-tight seal of adequate strength between cannulas or between valves other devices and cannulas. For example, U.S. Pat. No. 5,084,031 to Todd, et. al., Jan. 28, 1992, discloses a device in which a plane right cylindrical tube is used to connect a valving device to a cannula. This is entirely satisfactory in many applications—provided the tube on the valve is of the proper size to mate with the cannula to form a liquid tight seal of adequate strength. Therein, however, lies the problem.

It is not economically feasible to manufacture a series of complex or expensive devices which differ only as to outlet or inlet tube size. Even if such devices could be manufactured economically, having a full array of different sized devices in the operating room conveniently accessible to the surgeon is not practicable.

Frequently, the surgeon needs to shunt blood or fluid flow from one size vessel to a different size vessel. While special fittings can be, and are, available, the need to anticipate the need for various sizes and to have them on hand in the operating room is an added complexity.

It is to this problem that the present invention is addressed.

SUMMARY OF THE INVENTION

A multi-diameter, multi-purpose cannula-to-vessel connector, which may be in the form of a shunt, occluder, or perfusion cannula intended for use as an aid in the execution of selected cardiovascular surgical procedures is described and claimed here.

The present invention has specific application in coronary artery bypass graft surgery. It is common surgical practice to use bypass grafts to help reestablish coronary artery circulation. In most patients one or usually more segments of the saphenous vein taken from the patient's legs will be implanted between the aorta near its base and just distal to the blockage of the branch of the stenosed coronary artery.

In some patients, the internal mammary artery is also utilized for bypassing the most important coronary artery which is stenosed. The aorta is cross clamped during the period of actual coronary artery surgery to minimize bleeding from the anastomotic sites of the coronary arteries. However, when an incision is made into the stenotic coronary artery a significant amount of hemorrhage may occur. The hemorrhage is thought to be due to the presence of collateral circulatory channels, probable emanating from the bronchial arteries. In such circumstances the surgeon's delicate task of producing a competent, yet leak tight, anastomosis between the bypass graft and the semi-occluded vessel in a reasonably short time, is made difficult.

Vessel occluders are known in the art. For example Mullen, D. C., Lepley, D. Jnr., and Flemma, R. J. described the use of a coronary occluder in their paper "Coronary artery surgery without global ischemia." (Ann Thorac Surg 24:90, 1977. This device is a "T" shaped device with a bulbous tip placed at either end of the "T". The device was manufactured from silicon rubber. A similar device, the Florester® coronary artery occluder is presently produced, and described in a brochure, by Bio-Vascular, Inc. St Paul, Minn. The device which is the subject of this invention does not have these disadvantages.

It is an objective of this invention to provide a vessel shunt that may be used with vessels of various diameters.

It is a further objective of this invention to provide a vessel occluder that may be used with vessels of various diameters.

It is a further objective of this invention to provide a vessel perfusion cannula that may be used with vessels of various diameters.

The simplicity and design of the multudiameter, multi-purpose vessel shunt, occluder and perfusion cannula are such that it is quite inexpensive and hence may be disposable, hereby eliminating the necessity of cleaning and sterilizing between uses.

In a specific sense, this invention is directed to a multi-diameter, multi-purpose vessel shunt, occluder and perfusion cannula vessel occluder comprising one or several small flexible cannulas each with several circumferential flanges, spaced a short distance apart and located near the proximal end of the cannula. The outside diameters of the flanges are graduated such the largest diameter flange lies near the proximal end of the cannula, while the smallest diameter flange lies most distal from the proximal end of the cannula. Intermediate diameter flanges are located between the largest and smallest flange such that larger diameter intermediate flanges lie proximate to the largest flange and smaller diameter intermediate flanges lie between the largest and smallest flange but closest to the smallest flange. Thus the largest flange lies close to the proximal end of the cannula, the next smaller flange lies near the largest flange, next lies the next smaller flange, and so on until the smallest flange which is the flange most distal from the proximal end of the cannula.

The distal ends of the cannula are, typically, terminated with Luer fittings, although the distal end may terminate in any fitting or connected to a valve or other device. The cannula may by attached to a multi-way (usually four-way) stopcock. Guide members may be introduced into the cannula to provide sufficient rigidity to allow the cannula to be introduced into the vessel.

In a preferred embodiment, the present invention is cannula-to-vessel connector or occluder that comprises an elongate cylindrical member having an external cylindrical surface of a predetermined diameter and having first and second spaced apart ends, and connector means on the first end for connection to a tube or blood vessel or vein, said connector means comprising a tip portion of substantially the same diameter as said predetermined diameter and, spaced closely adjacent said tip portion, a plurality of circumferential flanges of different diameters spaced a short distance apart from each other, said flanges being configured, dimensioned and constructed such that the largest diameter flange lies immediately adjacent the tip portion and the smallest diameter flange lies more distant from the tip portion than the largest diameter flange, said flanges being configured, dimensioned and constructed such that the diameters of the flanges are larger than the diameter of said closely adjacent tip portion and preferably comprises an intermediate diameter flange located between said largest and said smallest flanges.

In another preferred embodiment, the invention is a cannula-to-vessel connector or occluder that comprises an elongate cannula having a first external cylindrical surface of a first predetermined diameter a first end, a second external cylindrical surface of a second predetermined diameter a second end, and connector means on said first end for connection to a tube or blood vessel or vein, said connector means comprising a tip portion of substantially the same diameter as said predetermined diameter and, spaced closely adjacent said tip portion, a plurality of circumferential flanges of different diameters spaced a short distance apart from each other, said flanges being configured, dimensioned and constructed such that the largest diameter flange lies immediately adjacent the tip portion and the smallest diameter flange lies more distant from the tip portion than the largest diameter flange, said flanges being configured, dimensioned and constructed such that the diameters of the flanges are larger than the diameter of said closely adjacent tip portion.

BRIEF DESCRIPTION OF THE DRAWINGS

The following drawings are provided solely to illustrate the invention but, of course, the invention is not limited to the specific structures or devices shown in the drawings for the purpose of illustrating the invention. This invention is not limited to the precise arrangements and instrumentalities shown; rather, the invention can be embodied into virtually any cannula used for connection to a vessel.

FIGS. 1a and 1b are, respectively, cross-sectional and plan views of the multi-diameter, multi-purpose vessel connector of this invention for connecting to a small vessel.

FIGS. 2a and 2b are, respectively, cross-sectional and plan views of the multi-diameter, multi-purpose vessel connector of this invention for connecting to an intermediate vessel.

FIGS. 3a and 3b are, respectively, cross-sectional and plan views of the multi-diameter, multi-purpose vessel connector of this invention for connecting to a large vessel.

FIG. 4 is and enlarged cross-sectional view of the first end of a typical multi-diameter, multi-purpose vessel connector showing, by way of example, three circumferential flanges, spaced a short distance apart and located near the proximal end of the cannula and a stiffener S inside the cannula, and an angled line "L" added simply to emphasize the increasing size of the flanges from the distal toward the proximal end of the cannula.

DESCRIPTION OF THE PREFERRED EMBODIMENTS

The following description is of exemplary embodiments intended, along with the drawings, to illustrate the principles of the invention and is not a limitation of the usage, application or scope of the invention.

Referring first to FIGS. 1a and 1b, a cannula structure 10 with a Luer connector on the second end is shown. In this depiction, as in all depictions, the Luer is simply exemplary of the device that may be attached to or form the second end of the cannula. In the example in FIGS. 1, the cannula tapers as shown at 14 to a smaller cannula portion. The connector portion is on the proximal end, also called the first of the cannula in the form of plural flanges adjacent the proximal or first end of the cannula as shown at 16, 18 and 20, by way of example. Obviously more than three flanges may be so formed if desired. The outside diameters of the respective flanges are graduated such that the largest diameter flange 16 lies near the proximal end of the cannula, while the smallest diameter flange 20 lies most distal from the tip of the first end of the cannula. Intermediate diameter flanges, such as 18 for example, are located between the largest and smallest flange such that larger diameter intermediate flanges lie proximate to the largest flange and smaller diameter intermediate flanges lie between the largest and smallest flange but closest to the smallest flange. Thus, regardless of the number of flanges, the largest flange lies close to the proximal or first end of the cannula, the next smaller flange lies near the largest flange, next lies the next smaller flange, and so on until the smallest flange which is the flange most distal from the proximal or first end of the cannula.

Referring first to FIGS. 2a and 2b, a cannula structure 30 with a Luer connector on the distal end is shown. In this depiction, as in all depictions, the Luer is simply exemplary of the device that may be attached to or form the distal end of the cannula. The connector portion is on the proximal end of the cannula in the form of plural flanges adjacent the proximal end of the cannula as shown at 36, 38 and 40, by way of example. Obviously more than three flanges may be so formed if desired. The outside diameters of the respective flanges are graduated such that the largest diameter flange 36 lies near the proximal end of the cannula, while the smallest diameter flange40 lies most distal from the proximal end of the cannula. Intermediate diameter flanges, such as 38 for example, are located between the largest and smallest flange such that larger diameter intermediate flanges lie proximate to the largest flange and smaller diameter intermediate flanges lie between the largest and smallest flange but closest to the smallest flange. Thus, regardless of the number of flanges, the largest flange lies close to the proximal end of the cannula, the next smaller flange lies near the largest flange, next lies the next smaller flange, and so on until the smallest flange which is the flange most distal from the proximal end of the cannula.

Referring first to FIGS. 3a and 3b, a cannula structure 50 with a Luer connector on the distal end is shown. In this depiction, as in all depictions, the Luer is simply exemplary of the device that may be attached to or form the distal end of the cannula. In the example in FIGS. 3, the cannula tapers as shown at 54 to a smaller cannula portion. The connector portion is on the proximal end of the cannula in the form of plural flanges adjacent the proximal end of the cannula as shown at 56, 58 and 60, by way of example. Obviously more than three flanges may be so formed if desired. The outside diameters of the respective flanges are graduated such that the largest diameter flange 56 lies near the proximal end of the cannula, while the smallest diameter flange 60 lies most distal from the proximal end of the cannula. Intermediate diameter flanges, such as 58 for example, are located between the largest and smallest flange such that larger diameter intermediate flanges lie proximate to the largest flange and smaller diameter intermediate flanges lie between the largest and smallest flange but closest to the smallest flange. Thus, regardless of the number of flanges, the largest flange lies close to the proximal end of the cannula, the next smaller flange lies near the largest flange, next lies the next smaller flange, and so on until the smallest flange which is the flange most distal from the proximal end of the cannula.

While specific dimensions are not critical to the invention, it is contemplated that two, three or four connectors will be provided together. In the example shown, three connectors are provided. By way of example only, the outer diameters of the flanges are 1.0 mm, 1.25 mm and 1.5 mm in FIGS. 1; 2.0 mm, 2.25 mm and 2.75 mm in FIGS. 2, and 3.0 mm, 4.5 mm and 6.0 mm in FIGS. 3. The same size range can, of course be covered in fewer or more cannula as desired.

Use of the invention in the operating room is simple and efficient. The surgeon can usually estimate visually the approximate size of connector that will be required for a given vessel and can select a connector that will span the estimated size range. The connector is then attempted to be inserted into the vessel. If it fits snugly inside and slightly stretches the vessel to form a liquid tight and satisfactory seal, then the surgeon proceeds to the next step. If, however, the connector is too large, the surgeon simply snips of the larger flange and uses the next flange, proceeding seriatim until the proper cannula-to-vessel connection is formed.

The cannula-to-vessel connector may very conveniently be used in vessel shunts, and in occluding and perfuming devices. The invention is suitable for use in a coronary artery anastomoses.

In use, following commencement of cardio-pulmonary bypass the heart will usually be immobilized by cross clamping the base of the aorta, and perfusing cold cardioplegia solution into the coronary arteries via the aortic root. The surgeon makes a suitable incision into the lumen of the coronary artery to be bypassed, distal to the coronary occlusion, and elongates the incision as required. A coronary probe is then inserted into the vessel to check for occlusions, and to estimate the diameter of the lumen of the vessel. The appropriate size of coronary cannula is selected. The size selected will be such that the connector flange may be gently but firmly inserted into the lumen of the artery. Using atraumatic forceps to grip the cannula close to the flanges, the cannula is pushed into the exposed lumen, slightly past the area of the incision. The firmly fitting flange will prevent leakage and hemorrhage from the artery, and serve to hold the vessel in a circular configuration, thus improving exposure for the surgeon to place the anastomotic sutures. Once in place the cannula may be used to perfuse the vessel, or if terminated at the distal end by a closed stopcock, will act as an occluder. The anastomosis of the saphenous vein or the internal mammary artery is carried out in the usual manner. Prior to completing the anastomosis by tying off the anastomotic suture, each cannula is, in turn, gently removed using atraumatic forceps to grip the cannula in a suitable place, and pulling gently. The devices may be provided with occludes of sizes appropriate to surgical demands. The instrumentation required for proper size selection of these vessel occluders consists of vessel probes. These cardiovascular surgical instruments are available in suitable sizes and have been used routinely in coronary artery surgery for many years.

Referring momentarily to FIG. 4, it will be understood that in the foregoing and in all procedures, the surgeon may insert a stiffener S inside the cannula to aid in inserting the cannula into the vessel. The stiffener S may be of any biocompatible construction and material. Soft metal or resilient metal, moderate rigidity polymeric material, etc. may be used. Whether or not to use a stiffener is a function of the type of surgery, the accessibility of the vessel in to which the cannula is to be inserted and the preference of the surgeon. Thus, use of a stiffener is not an integral or necessary aspect of this invention. The stiffener is smaller than the internal diameter of the annulus and is configured and constructed so as to be removable once the annulus is conducted.

With brief continued reference to FIG. 4, note that the added line L diverges from the cannula from distal to proximal. This illustration is to emphasize the arrangement of the flanges and does not necessarily indicate that a pencil of lines drawn on the perimeters of the flanges would define a cone. Such may be the relationship of the flanges, but if so would simply be a coincidence.

The principal of the invention is embodied, in one form, in the provision of a multi-diameter, multi-purpose cannula to vessel connector or occluder that comprises a cannula having plural circumferential flanges spaced a short distance apart and located near the proximal end of the cannula, the outside diameters of the flanges being graduated such the largest diameter flange lies near the proximal end of the cannula, while the smallest diameter flange lies most distal from the proximal end of the cannula and intermediate diameter flanges located between the largest and smallest flange such that larger diameter intermediate flanges lie proximate to the largest flange and smaller diameter intermediate flanges lie between the largest and smallest flange but closet to the smallest flange. Thus the largest flange lies close to the proximal end of the cannula, the next smaller flange lies near the largest flange, next lies the next smaller flange, and so on until the smallest flange which is the flange most distal from the proximal end of the cannula. The same structure, i.e. the plural flanges as described, can be formed on a solid member, equivalent in function and structure, of course, to a cannula, such as a bar or pin, if plugging the vessel is desired. Other variations will be apparent to those skilled in the art.

INDUSTRIAL APPLICATION

This invention is useful in the medical and surgical instrument industries.

What is claimed is:

1. A vessel connector or occluder that comprises an elongate cylindrical member having an external cylindrical surface of a predetermined diameter and having first and second spaced apart ends, and connector means on the first end for connection to a tube or blood vessel or vein, said connector means comprising a tip portion of substantially the same diameter as said predetermined diameter and, spaced closely adjacent said tip portion, a plurality of circumferential flanges of different diameters spaced a short distance apart from each other, said flanges being configured, dimensioned and constructed such that the largest diameter flange lies immediately adjacent the tip portion and the smallest diameter flange lies more distant from the tip portion than the largest diameter flange, said flanges being configured, dimensioned and constructed such that the diameters of the flanges are larger than the diameter of said closely adjacent tip portion.

2. The invention of claim 1 further comprising an intermediate diameter flange located between said largest and said smallest flanges.

3. A cannula-to-vessel connector or occluder that comprises an elongate cannula having a first external cylindrical surface of a first predetermined diameter a first end, a second external cylindrical surface of a second predetermined diameter a second end, and connector means on said first end for connection to a tube or blood vessel or vein, said connector means comprising a tip portion of substantially the same diameter as said predetermined diameter and, spaced closely adjacent said tip portion, a plurality of circumferential flanges of different diameters spaced a short distance apart from each other, said flanges being configured, dimensioned and constructed such that the largest diameter flange lies immediately adjacent the tip portion and the smallest diameter flange lies more distant from the tip portion than the largest diameter flange, said flanges being configured, dimensioned and constructed such that the diameters of the flanges are larger than the diameter of said closely adjacent tip portion.

4. The invention of claim 3 further comprising an intermediate diameter flange located between said largest and said smallest flanges.

5. The invention of claim 1 wherein said second end is dimensioned and constructed in a configuration different from the first end.

* * * * *